US009962345B2

(12) United States Patent
Singh et al.

(10) Patent No.: US 9,962,345 B2
(45) Date of Patent: *May 8, 2018

(54) ORAL LIQUID COMPOSITIONS OF GUANFACINE

(71) Applicant: SUN PHARMACEUTICAL INDUSTRIES LIMITED, Mumbai, Maharashtra (IN)

(72) Inventors: Romi Barat Singh, Varanasi (IN); Kalaiselvan Ramaraju, Trichirapalli (IN); Balaram Mondal, East Midnapore (IN); Ashish Kumar, Jhajjar (IN); Suchitra Kaushik, Haridwar (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/144,026

(22) Filed: May 2, 2016

(65) Prior Publication Data

US 2016/0346235 A1    Dec. 1, 2016

Related U.S. Application Data

(63) Continuation-in-part of application No. 15/133,826, filed on Apr. 20, 2016, which is a continuation of application No. PCT/IB2015/053209, filed on May 1, 2015.

(30) Foreign Application Priority Data

May 1, 2014    (IN) .......................... 1183/DEL/2014

(51) Int. Cl.
| | |
|---|---|
| *A61K 9/00* | (2006.01) |
| *A61K 9/10* | (2006.01) |
| *A61K 31/17* | (2006.01) |
| *A61K 9/14* | (2006.01) |
| *A61K 9/50* | (2006.01) |
| *A61K 31/155* | (2006.01) |
| *A61K 31/165* | (2006.01) |
| *A61K 31/43* | (2006.01) |
| *A61K 31/4439* | (2006.01) |
| *A61K 31/522* | (2006.01) |
| *A61K 9/16* | (2006.01) |

(52) U.S. Cl.
CPC ............ *A61K 31/17* (2013.01); *A61K 9/0053* (2013.01); *A61K 9/0095* (2013.01); *A61K 9/10* (2013.01); *A61K 9/145* (2013.01); *A61K 9/1652* (2013.01); *A61K 9/1676* (2013.01); *A61K 9/501* (2013.01); *A61K 9/5015* (2013.01); *A61K 9/5026* (2013.01); *A61K 9/5031* (2013.01); *A61K 9/5042* (2013.01); *A61K 9/5047* (2013.01); *A61K 9/5078* (2013.01); *A61K 9/5084* (2013.01); *A61K 9/5089* (2013.01); *A61K 31/155* (2013.01); *A61K 31/165* (2013.01); *A61K 31/43* (2013.01); *A61K 31/4439* (2013.01); *A61K 31/522* (2013.01)

(58) Field of Classification Search
CPC ........................... A61K 9/0095; A61K 9/0053
See application file for complete search history.

(56) References Cited

U.S. PATENT DOCUMENTS

| | | | |
|---|---|---|---|
| 3,156,369 A | 11/1964 | Bowes et al. | ..................... 215/6 |
| 3,603,469 A | 9/1971 | Magni | .................... 215/6 |
| 3,632,645 A | 1/1972 | Bream et al. | ................ 260/558 |
| 3,840,136 A | 10/1974 | Lanfranconi et al. | ............ 215/6 |
| 4,024,952 A | 5/1977 | Leitz | |
| 4,982,875 A | 1/1991 | Pozzi et al. | ..................... 222/83 |
| 5,058,770 A | 10/1991 | Herold et al. | .................. 222/80 |
| 5,273,760 A | 12/1993 | Oshlack et al. | ............. 424/480 |
| 5,419,445 A | 5/1995 | Kaesemeyer | ................ 215/11.1 |
| 5,431,915 A | 7/1995 | Harvey et al. | ................ 424/439 |
| 5,460,828 A | 10/1995 | Santus et al. | |
| 5,472,712 A | 12/1995 | Oshlack et al. | ............. 424/480 |
| 5,854,290 A | 12/1998 | Arnsten et al. | ............... 514/617 |
| 6,148,996 A | 11/2000 | Morini | ......................... 206/222 |
| 6,156,340 A | 12/2000 | Adeyeye et al. | ............. 424/463 |
| 6,287,599 B1 | 9/2001 | Burnside et al. | ............. 424/468 |
| 6,676,966 B1 | 1/2004 | Odidi et al. | .................. 424/464 |
| 6,811,794 B2 | 11/2004 | Burnside et al. | ............. 424/468 |
| 6,890,957 B2 | 5/2005 | Chandran et al. | ............ 514/634 |

(Continued)

FOREIGN PATENT DOCUMENTS

| | | | |
|---|---|---|---|
| EP | 0 601 508 B1 | 3/1999 | |
| EP | 1 140 027 | 10/2005 | ............... A61K 9/16 |

(Continued)

OTHER PUBLICATIONS

Kristine, "EKG Results/ Tenex", Dr. Mom's Spot, Mar. 26, 2010, http://drmomsspot.blogspot.com/2010/03/ekg-results-tenex.html.*
Steeman, 2009. Innovative dispensing bottle caps for sensitive vitamins [online]. Best in Packaging. Available from: http://bestinpackaging.com/2009/05/29/innovative-dispensing-bottle-caps-for-sensitive-vitamins/.
Co-pending PCT Application No. PCT/IB2015/053209 filed May 1, 2015.
International Search Report and Written Opinion for International Application No. PCT/IB2015/053209, issued by PCT dated Aug. 14, 2015.

(Continued)

*Primary Examiner* — Gina C Justice
(74) *Attorney, Agent, or Firm* — Liang, Frank & King, LLP; Stanley D. Liang

(57) ABSTRACT

The present invention relates to oral liquid compositions of guanfacine. The liquid compositions can be immediate release or extended release compositions. The compositions comprise guanfacine in a concentration from about 0.1 mg/mL to about 12.0 mg/mL of the composition. The liquid compositions can be in the form of ready-to use liquid compositions or reconstituted liquid compositions. It further relates to processes for the preparation of said oral liquid compositions.

12 Claims, No Drawings

(56) References Cited

U.S. PATENT DOCUMENTS

| | | | | |
|---|---|---|---|---|
| 7,214,387 | B2 | 5/2007 | Sanghvi et al. | 424/468 |
| 7,906,145 | B2 | 3/2011 | Castan et al. | 424/489 |
| 8,002,734 | B2 | 8/2011 | Bassarab et al. | 604/82 |
| 8,197,850 | B2 | 6/2012 | Castan et al. | 424/489 |
| 8,297,456 | B1 | 10/2012 | Anderson | 215/227 |
| 8,318,210 | B2 | 11/2012 | Tengler et al. | 424/501 |
| 8,453,833 | B2 | 6/2013 | Porter | |
| 8,491,935 | B2 | 7/2013 | Mehta et al. | 424/487 |
| 8,541,018 | B2 | 9/2013 | Radke et al. | 424/439 |
| 8,960,424 | B1 | 2/2015 | Anderson | |
| 9,132,950 | B1 | 9/2015 | Anderson et al. | |
| 2001/0032643 | A1 | 10/2001 | Hochrainer et al. | 128/200.21 |
| 2003/0171407 | A1 | 9/2003 | Freese et al. | 514/342 |
| 2003/0199846 | A1 | 10/2003 | Fowles et al. | 604/403 |
| 2004/0062800 | A1 | 4/2004 | Burnside et al. | 424/468 |
| 2004/0062802 | A1 | 4/2004 | Hermelin | 424/468 |
| 2004/0109891 | A1 | 6/2004 | Sanghvi et al. | 424/468 |
| 2007/0193894 | A1 | 8/2007 | Macken et al. | 206/219 |
| 2008/0008765 | A1 | 1/2008 | Schwarz et al. | 424/493 |
| 2008/0095855 | A1* | 4/2008 | Schwarz | A61K 9/0095 424/490 |
| 2008/0118570 | A1 | 5/2008 | Liu et al. | 424/490 |
| 2008/0124432 | A1 | 5/2008 | Ma | |
| 2008/0202950 | A1 | 8/2008 | Anderson | 206/219 |
| 2008/0314775 | A1 | 12/2008 | Owoc | |
| 2009/0123538 | A1 | 5/2009 | Alani et al. | 424/464 |
| 2009/0142378 | A1 | 6/2009 | Frisbee | 424/400 |
| 2009/0176691 | A1 | 7/2009 | Bennis et al. | 514/3 |
| 2009/0325938 | A1 | 12/2009 | Lichter et al. | 514/220 |
| 2010/0092562 | A1 | 4/2010 | Hollenbeck et al. | 424/488 |
| 2010/0282624 | A1 | 11/2010 | Paganuzzi | |
| 2010/0330150 | A1 | 12/2010 | Venkatesh et al. | 424/439 |
| 2011/0313046 | A1 | 12/2011 | Ermer | 514/617 |
| 2012/0178666 | A1* | 7/2012 | Franklin | C07C 279/24 514/1.3 |
| 2012/0220930 | A1 | 8/2012 | Griffiths et al. | 604/89 |
| 2013/0109659 | A1 | 5/2013 | Soler Ranzani et al. | 514/158 |
| 2014/0050796 | A1* | 2/2014 | Tengler | A61K 9/0056 424/494 |
| 2014/0319141 | A1 | 10/2014 | Stratis et al. | 220/277 |
| 2015/0021214 | A1 | 1/2015 | Besic et al. | |

FOREIGN PATENT DOCUMENTS

| | | | | |
|---|---|---|---|---|
| WO | WO 00/38655 | 7/2000 | | A61K 9/16 |
| WO | WO 2006/030297 | 3/2003 | | A61K 9/16 |
| WO | WO 2008/122993 | 10/2008 | | A61K 9/16 |
| WO | WO 2011/077451 | 6/2011 | | A61K 9/28 |
| WO | WO 2011/107855 | 9/2011 | | A61K 9/50 |
| WO | WO 2011/150506 | 12/2011 | | A61K 9/48 |
| WO | WO 2012/063257 | 5/2012 | | A61K 47/30 |
| WO | WO 2014/174119 | 10/2014 | | A61K 31/155 |

OTHER PUBLICATIONS

International Preliminary Report on Patentability for International Application No. PCT/IB2015/053209, issued by PCT dated Nov. 10, 2016.
Co-pending U.S. Appl. No. 15/133,826, filed Apr. 20, 2016.
Office Action for U.S. Appl. No. 15/133,826, issued by USPTO dated Jul. 28, 2016.
Co-pending PCT Application No. PCT/IB2016/052604 filed May 6, 2016.
International Search Report and Written Opinion for International Application No. PCT/IB62016/052604, issued by PCT dated Aug. 31, 2016.
Co-pending U.S. Appl. No. 15/148,069, filed May 6, 2016.
Office Action for U.S. Appl. No. 15/148,069, issued by USPTO dated Nov. 2, 2016.
Co-pending PCT Application No. PCT/IB2016/052607 filed May 6, 2016.
International Search Report and Written Opinion for International Application No. PCT/IB2016/052607, issued by PCT dated Sep. 2, 2016.
Co-pending U.S. Appl. No. 15/148,131, filed May 6, 2016.
Office Action for U.S. Appl. No. 15/148,131, issued by USPTO dated Oct. 7, 2016.
Co-pending PCT Application No. PCT/IB2016/052485 filed May 2, 2016.
International Search Report and Written Opinion for International Application No. PCT/IB2016/052485, issued by PCT dated Aug. 31, 2016.
Co-pending PCT Application No. PCT/IB2015/055780 filed Jul. 30, 2015.
International Search Report and Written Opinion for International Application No. PCT/IB2015/055780, issued by PCT dated Dec. 7, 2015.
Co-pending PCT Application No. PCT/IB2016/052486 filed May 2, 2016.
International Search Report and Written Opinion for International Application No. PCT/IB2016/052486, issued by PCT dated Sep. 9, 2016.
Co-pending U.S. Appl. No. 15/144,058, filed May 2, 2016.
Co-pending U.S. Appl. No. 15/352,993, filed Nov. 16, 2016.
Lopez-Liuchi et al., "Therapy for type 2 diabetes: where do we stand after the UK Prospective Diabetes Study?," *European Journal of Endocrinology*, 140:4-6 (1999).
Murtaza,"Ethylcellulose Microparticles: A Review," *Drug Research*, 69(1):11-22 (2012).
Co-pending PCT Application No. PCT/IB2015/053207 filed May 1, 2015, published as WO 2015/166472 on Nov. 5, 2015.
International Search Report and Written Opinion for International Application No. PCT/IB2015/053207, issued by US/ISA dated Aug. 7, 2015.
International Preliminary Report on Patentability for International Application No. PCT/IB2015/053207, issued by WIPO dated Mar. 16, 2016.
Co-pending U.S. Appl. No. 15/133,773, filed Apr. 20, 2016, published as U.S. 2016/0228360 on Aug. 11, 2016.
Restriction Requirement for U.S. Appl. No. 15/133,773, issued by USPTO dated Jun. 10, 2016.
Office Action for U.S. Appl. No. 15/133,773, issued by USPTO dated Jul. 27, 2016.
Final Office Action for U.S. Appl. No. 15/133,773, issued by USPTO dated Dec. 16, 2016.
Final Office Action for U.S. Appl. No. 15/133,773, issued by USPTO dated Apr. 13, 2017.
Co-pending PCT Application No. PCT/IB2016/052484 filed May 2, 2016, published as WO 2016/178130 dated Nov. 10, 2016.
International Search Report and Written Opinion for International Application No. PCT/IB2016/052484, issued by US/ISA dated Sep. 8, 2016.
Co-Pending U.S. Appl. No. 15/144,000, filed May 2, 2016, not yet published.
Office Action for U.S. Appl. No. 15/144,000, issued by USPTO dated Jun. 23, 2016.
Final Office Action for U.S. Appl. No. 15/144,000, issued by USPTO dated Nov. 4, 2016.
Office Action for U.S. Appl. No. 15/144,000, issued by USPTO dated Feb. 14, 2017.
Restriction Requirement for U.S. Appl. No. 15/133,826, issued by USPTO dated Jun. 23, 2016.
Final Office Action for U.S. Appl. No. 15/133,826, issued by USPTO dated Dec. 20, 2016.
Office Action for U.S. Appl. No. 15/133,826, issued by USPTO dated Feb. 14, 2017.
Restriction Requirement for U.S. Appl. No. 15/148,069, issued by USPTO dated Jul. 21, 2016.
Final Office Action for U.S. Appl. No. 15/148,069, issued by USPTO dated Mar. 20, 2017.
Final Office Action for U.S. Appl. No. 15/148,131, issued by USPTO dated Apr. 5, 2017.
International Preliminary Report on Patentability for International Application No. PCT/IB2015/055780, issued by US/ISA dated Feb. 9, 2017.

(56) References Cited

OTHER PUBLICATIONS

Co-pending U.S. Appl. No. 15/329,070, filed Jan. 25, 2017, not yet published.
Restriction Requirement for U.S. Appl. No. 15/144,058, issued by USPTO dated Sep. 30, 2016.
Office Action for U.S. Appl. No. 15/144,058, issued by USPTO dated Dec. 16, 2016.
Office Action for U.S. Appl. No. 15/144,058, issued by USPTO dated May 11, 2017.
Office Action for U.S. Appl. No. 15/352,993, issued by USPTO dated Mar. 24, 2017.
Co-pending PCT Application No. PCT/IB2016/052488 filed May 2, 2016, not yet published.
International Search Report and Written Opinion for International Application No. PCT/IB2016/052488, issued by US/ISA dated Aug. 31, 2016.
Co-pending U.S. Appl. No. 15/144,098, filed May 2, 2016, not yet published.
Medela Breast Milk Bottle Set, Target, published on or before 2010. Available from: www.target.com/p/medela-breast-milk-set-8oz-3ct/-/A-11189915 (Accessed on: Aug. 14, 2017).
Final Office Action for U.S. Appl. No. 15/144,058, issued by USPTO dated Jul. 21, 2017.
Office Action for U.S. Appl. No. 15/144,098, issued by USPTO dated Jul. 13, 2017.
Office Action for U.S. Appl. No. 15/133,773, issued by USPTO dated Aug. 1, 2017.
Office Action for U.S. Appl. No. 15/148,069, issued by USPTO dated Aug. 10, 2017.
Office Action for U.S. Appl. No. 15/352,993, issued by USPTO dated Aug. 24, 2017.
Final Office Action for U.S. Appl. No. 15/144,000, issued by USPTO dated Aug. 24, 2017.
Intuiv: Highlights of prescribing information (201 X Shire US Inc, Revised Feb. 2013).
Office Action for U.S. Appl. No. 15/148,131, issued by USPTO dated Sep. 29, 2017.

* cited by examiner

ORAL LIQUID COMPOSITIONS OF GUANFACINE

FIELD OF THE INVENTION

The present invention relates to oral liquid compositions of guanfacine. The liquid compositions can be immediate release or extended release compositions. The compositions comprise guanfacine in a concentration from about 0.1 mg/mL to about 12.0 mg/mL of the composition. The liquid compositions can be in the form of ready-to use liquid compositions or reconstituted liquid compositions. It further relates to processes for the preparation of said oral liquid compositions.

BACKGROUND OF THE INVENTION

Guanfacine is a central alpha$_{2A}$-adrenergic receptor agonist indicated for the treatment of Attention Deficit Hyperactivity Disorder (ADHD) as monotherapy and as adjunctive therapy to stimulant medications. It is also indicated is indicated in the management of hypertension, either alone or in combination with other antihypertensive agents, especially thiazide-type diuretics. Guanfacine hydrochloride, a pharmaceutically acceptable salt of guanfacine, is a white to off-white crystalline powder, sparingly soluble in water (approximately 1 mg/mL) and alcohol and slightly soluble in acetone. The chemical designation for guanfacine hydrochloride is N-amidino-2-(2,6-dichlorophenyl)-acetamide monohydrochloride. The chemical structure is:

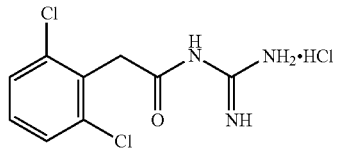

Guanfacine and its pharmaceutically acceptable salts is disclosed in U.S. Pat. No. 3,632,645. U.S. Pat. No. 5,854,290 discloses the method of treating a behavioral disinhibition (e.g. Attention-Deficit Hyperactivity Disorder) in a primate with minimal sedative side effects by administering thereto a therapeutically effective amount of guanfacine.

U.S. Pat. Nos. 6,287,599 and 6,811,794 describe sustained release tablet compositions of guanfacine, comprising at least one non-pH dependent sustained release agent; and at least one pH dependent agent that increases the rate of release of guanfacine from the tablet at a pH in excess of 5.5.

Guanfacine is presently marketed only in solid dosage forms i.e. immediate release and extended release tablets for oral administration. However, solid dosage forms are not suitable for some patients who have difficulty in swallowing solid dosage forms e.g. pediatric patients or incapacitated patients. Further, solid dosage forms may not be convenient, when chronic therapy is needed. Therefore, there exists a clear need in the art for oral liquid compositions of guanfacine. To date, no liquid compositions of guanfacine are known. The only FDA approved guanfacine products are solid dosage forms i.e. tablets. In view of this, liquid compositions of guanfacine are desirable over presently available solid dosage forms, as they would offer better patient compliance, convenience and flexible dosing regimen.

However, a prime concern with any liquid formulation is the stability of the active ingredient, both short term and over the time. Inventors of the present application have for the first time developed oral liquid compositions of guanfacine. The compositions are stable both during manufacturing and shelf life. Said liquid compositions are suitable for both immediate release and extended release of guanfacine.

Therefore, the present invention is a significant advance over the available solid dosage forms of guanfacine and fulfills the long felt need to improve patient compliance by providing an oral liquid composition of guanfacine with acceptable stability.

Oral liquid compositions of guanfacine also offer additional advantages as are easy to manufacture with functional reproducibility. The oral liquid compositions described herein are provided with a pleasant mouth feel thereby further enhancing patient compliance and ease of administration.

SUMMARY OF THE INVENTION

The present invention relates to oral liquid compositions of guanfacine. The compositions comprise guanfacine in a concentration from about 0.1 mg/mL to about 12.0 mg/mL of the composition. Said liquid compositions are stable, in that, the amount of impurity 2,6-dichlorophenyl acetic acid in the composition is within the prescribed limits to the extent necessary for the sale and use of the composition.

The compositions are in the form of ready-to-use compositions or reconstituted liquid compositions. The compositions can be immediate release compositions or extended release compositions. Said compositions offer better patient compliance and dosing flexibility based on age and body weight of the patients. It also relates to processes for the preparation of said oral liquid compositions.

DETAILED DESCRIPTION OF THE INVENTION

A first aspect of the present invention provides an oral liquid composition comprising guanfacine in a pharmaceutically acceptable carrier.

A second aspect of the present invention provides an oral liquid composition comprising guanfacine in a pharmaceutically acceptable carrier, wherein the composition comprises guanfacine in a concentration from about 0.1 mg/mL to about 12.0 mg/mL of the composition. Particularly, the composition comprises guanfacine in a concentration from about 1.0 mg/mL to about 7.0 mg/mL of the composition.

A third aspect of the present invention provides an oral liquid composition comprising guanfacine in a pharmaceutically acceptable carrier, wherein the composition is a stable composition. Particularly, the composition is stable for at least seven days. More particularly, the composition is stable for at least one month or further, to the extent necessary for the sale and use of the composition.

According to one embodiment, the composition comprises less than about 1.0% w/w of 2,6-dichlorophenyl acetic acid. Particularly, the composition comprises less than about 0.7% w/w of 2,6-dichlorophenyl acetic acid.

According to another embodiment, the composition comprises less than about 3.0% w/w of total related substances. Particularly, the composition comprises less than about 2.0% w/w of total related substances.

A fourth aspect of the present invention provides an oral liquid composition comprising guanfacine in a pharmaceutically acceptable carrier, wherein the composition has a pH of less than about 6.8.

According to another embodiment of the above aspects, the composition is a taste-masked composition.

A fifth aspect of the present invention provides an oral liquid composition comprising guanfacine in a pharmaceutically acceptable carrier, wherein the composition is a ready-to-use liquid composition or a reconstituted liquid composition.

According to another embodiment, the ready-to-use liquid composition comprises a solution, a suspension, a syrup, a concentrate, an elixir or an emulsion.

According to another embodiment, the reconstituted liquid composition comprises a solution and/or a suspension reconstituted from powder comprising granules, pellets, or beads.

A sixth aspect of the present invention provides an oral liquid composition comprising guanfacine in a pharmaceutically acceptable carrier, wherein guanfacine is present in an immediate release form.

In above embodiments, guanfacine is present as powder, pellets, granules or beads, as guanfacine-resin complex, or as inert cores coated with guanfacine.

A seventh aspect of the present invention provides an oral liquid composition comprising guanfacine in a pharmaceutically acceptable carrier, wherein guanfacine is present in an extended release form.

In an embodiment of the above, the composition comprises:

(i) cores comprising guanfacine and a release-controlling agent; and (ii) a pharmaceutically acceptable carrier.

In one embodiment, guanfacine may be present in the core or layered over an inert particle to form a core.

In another embodiment, release-controlling agent may be present in the core or coated over the guanfacine core or both.

In another embodiment, the release-controlling agent is selected from the group comprising a pH-dependent release-controlling agent, a pH-independent release-controlling agent or mixtures thereof.

In another embodiment, the core further comprises one or more pharmaceutically acceptable excipients selected from the group comprising acids, osmogents, binders, glidants, or combinations thereof.

In another embodiment, the carrier comprises one or more of liquid adjuvants and other pharmaceutically acceptable excipients.

In another embodiment, the pharmaceutically acceptable excipients in the carrier are selected from the group comprising acids, osmogents, buffering agents, suspending agents, glidants, sweetening agents, flavors, colorants, anticaking agents, wetting agents, preservatives, antioxidants, chelating agents, binders, viscosity modifiers, and combinations thereof.

An eighth aspect of the present invention provides a method of treating Attention Deficit Hyperactivity Disorder or Hypertension by administering an oral liquid composition comprising guanfacine in a pharmaceutically acceptable carrier.

In an embodiment of the above aspect, the oral liquid composition is administered once daily.

The term "guanfacine", as used herein, refers to guanfacine, as well as its pharmaceutically acceptable salts, polymorphs, hydrates, solvates, prodrugs, chelates, and complexes. Exemplary salts include salts of inorganic or organic acids such as hydrochloride, hydrobromide, sulphate, sulfamate, nitrate, phosphate, formate, mesylate, citrate, benzoate, fumarate, maleate, tartrate, and succinate. A particularly preferred salt of guanfacine is guanfacine hydrochloride.

The oral liquid composition comprises guanfacine in a concentration from about 0.1 mg/mL to about 12.0 mg/mL of the composition. Preferably, the oral liquid composition comprises guanfacine in a concentration from about 1.0 mg/mL to about 7.0 mg/mL of the composition.

Guanfacine, particularly guanfacine hydrochloride, is found to degrade at high pH values. Solution state stability studies have indicated that at 16 hours, assay values of guanfacine have dropped down to 86.3% and 84% at pH 6.8 and 7.5 respectively and even further reduced at 24 hours. One of the major impurity of guanfacine is 2,6-dichlorophenyl acetic acid.

Inventors have surprisingly discovered that degradation of guanfacine can be prevented by maintaining the pH of the composition to less than about 6.8. In the present invention, the pH of the reconstituted liquid composition or ready-to-use liquid composition implies pH values measured for the pharmaceutically acceptable carrier, for the coated cores, or in the microenvironment of guanfacine, or combination of these that is sufficient to prevent degradation of guanfacine.

The term "stable," as used herein, refers to chemical stability, wherein the amount of impurity 2,6-dichlorophenyl acetic acid in the composition remains less than about 1.0%-w/w, particularly less than about 0.7% w/w upon storage of the composition for a period of at least seven days, more particularly, for a period of at least one month, or further, to the extent necessary for the sale and use of the composition.

The "liquid composition," includes ready-to-use liquid composition or reconstituted liquid composition. The ready-to-use liquid composition comprises a solution, a suspension, a syrup, a concentrate, an elixir or an emulsion or like. The reconstituted liquid compositions comprises solution and/or suspension reconstituted from dry powder comprising pellets, granules, beads or the like.

Guanfacine may be present in the above compositions in immediate release form, extended release form or combination of both.

As used herein, the term "immediate release," implies that guanfacine is released from the composition in an immediate release fashion and does not involve delayed release or extended release, but may include taste-masking.

When present in immediate release form, guanfacine may be present as powder, pellets, granules or beads. In one example, guanfacine, either alone or mixed with one or more of routinely used pharmaceutically acceptable excipients may be dissolved or dispersed in the pharmaceutically acceptable carrier.

In another example, guanfacine may be present as a resin complex that provides immediate release of guanfacine upon administration of the composition. These guanfacine-resin complexes are then dispersed in the pharmaceutically acceptable carrier as defined above. Cation- and anion-exchange resins are well-known in the art. Few exemplary resins that can be used according to the invention include, but are not limited to, Dowex® resins and others made by Dow Chemical; Amberlite®, Amberlyst® and other resins made by Rohm and Haas; Indion® resins made by Ion Exchange, Ltd. (India), Diaion® resins by Mitsubishi; Type AG® and other resins by BioRad; Sephadex® and Sepharose® made by Amersham; resins by Lewatit, sold by Fluka; Toyopearl® resins by Toyo Soda; IONAC® and Whatman® resins sold by VWR; and BakerBond® resins sold by J T Baker; hydrophilic colloids such as, alginate, chitosan, carboxymethylcellulose, croscarmellose, microcrystalline cellulose, xanthan gum; carboxy vinyl polymers such as carbomer 94, polylysine, gelatin; and resins having polymer backbones comprising styrene-divinyl benzene copolymers and having pendant ammonium or tetraalkyl ammonium functional groups, available from Rohm and Haas, sold under the trade name DUOLITE™ AP143; or any combinations thereof.

Alternatively, guanfacine may be present as coating over inert cores. These coated cores, optionally mixed with one or more pharmaceutically acceptable excipients are dispersed in a pharmaceutically acceptable carrier. The guanfacine coated core may be further optionally coated with a coating layer comprising a film-forming agent to mask the bitter taste or to improve the stability. The coating layer prevents guanfacine release during storage, but is quickly penetrated by gastric fluid allowing rapid release of guanfacine. In one example, the film-forming agent can be a water-soluble polymer in which the release of guanfacine is prevented by using a high molar concentration of the solutes in the reconstituted composition, wherein the solutes have a higher affinity towards water. The high molar concentration of the solutes generates hypertonic conditions leading to high osmolality and thus prevents the leaching of the guanfacine from the coated cores. Further, the film-forming agent can have a pH dependent solubility in which the release of active ingredient is prevented by using a pre-adjusted pH of the reconstituted composition such that the film-forming agent does not get dissolved in the reconstituted composition but get dissolved when exposed to the physiological conditions.

The term "inert particle," as used herein, refers to a particle made from a sugar sphere also known as a nonpareil seed, a microcrystalline cellulose sphere, a dibasic calcium phosphate bead, a mannitol bead, a silica bead, a tartaric acid pellet, a wax based pellet, and the like.

As used herein, the term "extended release," are used to define a release profile to effect delivery of guanfacine over an extended period of time, as being between about 60 minutes to about 2, 4, 6, 8, 12 or 24 hours. Extended release includes sustained release, controlled release, multiphase release, delayed release, pulsatile release, chrono release and the like.

When present in an extended release form, the composition comprises:
 (i) cores comprising guanfacine and a release-controlling agent; and
 (ii) a pharmaceutically acceptable carrier.

The cores may comprise guanfacine as powder, granules, and pellets. Alternatively, guanfacine may be layered over an inert particle to form a core. Alternatively, guanfacine may be present as a complex with a suitable complexing agent such as cyclodextrin, ion-exchange resins.

The core is in the form of a bead, pellet, granule, and spheroid or like.

The release-controlling agent is selected from the group comprising a pH-dependent release-controlling agent, a pH-independent release-controlling agent or mixtures thereof.

Suitable examples of pH-dependent release-controlling agents are selected from the group comprising acrylic copolymers such as methacrylic acid and methyl methacrylate copolymers, e.g., Eudragit® L 100 and Eudragit® S 100, methacrylic acid and ethyl acrylate copolymers, e.g., Eudragit® L 100-55 and Eudragit® L 30 D-55, dimethylaminoethyl methacrylate and butyl methacrylate and methyl methacrylate copolymers e.g., Eudragit® E 100, Eudragit® E PO, methyl acrylate and methacrylic acid and octyl acrylate copolymers, styrene and acrylic acid copolymers, butyl acrylate and styrene and acrylic acid copolymers, and ethylacrylate-methacrylic acid copolymer; cellulose acetate phthalate; cellulose acetate succinates; hydroxyalkyl cellulose phthalates such as hydroxypropylmethyl cellulose phthalate; hydroxyalkyl cellulose acetate succinates such as hydroxypropylmethyl cellulose acetate succinate; vinyl acetate phthalates; vinyl acetate succinate; cellulose acetate trimelliate; polyvinyl derivatives such as polyvinyl acetate phthalate, polyvinyl alcohol phthalate, polyvinyl butylate phthalate, and polyvinyl acetoacetal phthalate; zein; shellac; and mixtures thereof.

Suitable examples of pH-independent release-controlling agents are selected from the group comprising cellulosic polymers such as ethyl cellulose, methyl cellulose, hydroxyethyl cellulose, hydroxypropyl cellulose, hydroxyethylmethyl cellulose, hydroxypropylmethyl cellulose, cellulose acetate, and carboxy methylcellulose; acrylic copolymers such as methacrylic acid copolymers, e.g., Eudragit® RS, Eudragit® RL, Eudragit® NE 30 D; polyethylene derivatives e.g., polyethylene glycol and polyethylene oxide; polyvinyl alcohol; polyvinyl acetate; gums e.g., guar gum, locust bean gum, tragacanth, carrageenan, alginic acid, gum acacia, gum arabic, gellan gum, and xanthan gum; triglycerides; waxes, e.g., Compritol®, Lubritab®, and Gelucires®; lipids; fatty acids or their salts/derivatives; polyvinyl polymers; a mixture of polyvinyl acetate and polyvinyl pyrrolidone, e.g., Kollidon® SR; and mixtures thereof. In particular, the pH-independent polymer used in the present invention is ethyl cellulose.

The coating additives used in the present invention are selected from the group comprising plasticizers, opacifiers, anti-tacking agents, coloring agents, or combinations thereof.

Suitable plasticizers are selected from the group comprising triethyl citrate, dibutylsebacate, triacetin, acetylated triacetin, tributyl citrate, glyceryl tributyrate, diacetylated monoglyceride, rapeseed oil, olive oil, sesame oil, acetyl tributyl citrate, acetyl triethyl citrate, glycerin, sorbitol, diethyl oxalate, diethyl phthalate, diethyl malate, diethyl fumarate, dibutyl succinate, diethyl malonate, dioctyl phthalate, and mixtures thereof.

Suitable opacifiers are selected from the group comprising titanium dioxide, manganese dioxide, iron oxide, silicon dioxide, and mixtures thereof.

Suitable anti-tacking agents are selected from the group comprising talc, magnesium stearate, calcium stearate, stearic acid, silica, glyceryl monostearate, and mixtures thereof.

Suitable coloring agents are selected from the group consisting of FD&C (Federal Food, Drug and Cosmetic Act) approved coloring agents; natural coloring agents; natural juice concentrates; pigments such as iron oxide, titanium dioxide, and zinc oxide; and mixtures thereof.

Suitable solvents used for granulation or for forming a solution or dispersion for coating are selected from the group comprising water, ethanol, methylene chloride, isopropyl alcohol, acetone, methanol, and combinations thereof.

The diameter of the cores comprising guanfacine and a release-controlling agent has a $d_{90}$) value of less than about 1.5 mm. More particularly, $d_{90}$ value is less than 1.2 mm. It is desirable to keep the diameter of the cores within the specified size so as to avoid sedimentation of the cores, grittiness in the mouth and thereby rendering the composition more acceptable. The diameter of the cores is measured according to known methods, such as using Camsizer.

As used herein, the term "$d_{90}$ value," means at least 90% of the cores have volume diameter in the specified range when measured by a suitable method, for example, Camsizer.

Pharmaceutically acceptable carrier, constitutes the liquid part of the composition and comprises one or more of liquid adjuvants and other pharmaceutically acceptable excipients.

Suitable liquid adjuvants comprise water. It may optionally comprise a co-solvent, for example, propylene glycol, glycerol, sorbitol, and the like, to assist solubilization and incorporation of various water-insoluble ingredients, such as flavoring oils and the like, into the composition.

In certain embodiment, other pharmaceutically acceptable excipients in the carrier are selected from the group comprising acids, osmogents, buffering agents, suspending agents, glidants, sweetening agents, flavors, colorants, anticaking agents, wetting agents, preservatives, antioxidants, chelating agents, binders, viscosity modifiers, emulsifiers, and combinations thereof.

Suitable acids are selected from the group comprising organic acids, inorganic acids or mixtures thereof. Organic acids are selected from the group comprising citric acid, fumaric acid, tartaric acid, oxalic acid, succinic acid, adipic acid, phthalic acid, acetic acid, alginic acid, ascorbic acid, aspartic acid, benzoic acid, cyclamic acid, erythorbic acid, glutamic acid, hydrochloride, lactic acid, maleic acid, methacrylic acid, oleic acid, palmitic acid, sorbic acid, stearic acid, and combinations thereof inorganic acids are selected from the group comprising hydrochloric acid, hydrobromic acid, hydroiodic acid, nitric acid, phosphoric acid, sulfuric acid, boric acid, perchloric acid, and combinations thereof. Citric acid, fumaric acid, tartaric acid, ascorbic acid, benzoic acid, and hydrochloric acid are preferably used.

As used herein, the term "osmogents", refers to all pharmaceutically acceptable inert water-soluble compounds that can imbibe or dissolve in water and/or aqueous biological fluids. Suitable examples of osmogents or pharmaceutically acceptable inert water-soluble compounds are selected from the group comprising carbohydrates such as xylitol, mannitol, sorbitol, arabinose, ribose, xylose, glucose, fructose, mannose, galactose, sucrose, maltose, lactose, dextrose and raffinose; water-soluble salts of inorganic acids such as magnesium chloride, magnesium sulfate, potassium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, potassium dihydrogen phosphate, and sodium phosphate tribasic; water-soluble salts of organic acids such as sodium acetate, potassium acetate, magnesium succinate, sodium benzoate, sodium citrate, and sodium ascorbate; water-soluble amino acids such as glycine, leucine, alanine, methionine; urea or its derivatives; propylene glycol; glycerin; polyethylene oxide, xanthan gum, hydroxypropylmethyl cellulose; and mixtures thereof. Particularly, the osmogents used in the present invention are xylitol, mannitol, glucose, lactose, sucrose, and sodium chloride. Particularly, the osmogents used in the present invention are xylitol, mannitol, glucose, lactose, sucrose, and sodium chloride.

Suitable buffering agents are selected from the group comprising hydrochloric acid, citric acid, sodium citrate, potassium citrate, acetate buffer, sodium acetate trihydrate, potassium dihydrogen orthophosphate, trisodium hydrogen orthophosphate, sodium dihydrogen orthophosphate, disodium hydrogen orthophosphate, and mixtures thereof.

Suitable suspending agents are selected from the group comprising cellulose derivatives such as co-processed spray dried forms of microcrystalline cellulose and carboxymethyl cellulose sodium, hydroxypropyl cellulose, hydroxyethyl cellulose, hydroxypropylmethyl cellulose, methylcellulose, carboxymethyl cellulose and its salts/derivatives, and microcrystalline cellulose; carbomers; gums such as locust bean gum, xanthan gum, tragacanth gum, arabinogalactan gum, agar gum, gellan gum, guar gum, apricot gum, karaya gum, sterculia gum, acacia gum, gum arabic, and carrageenan; pectin; dextran; gelatin; polyethylene glycols; polyvinyl compounds such as polyvinyl acetate, polyvinyl alcohol, and polyvinyl pyrrolidone; sugar alcohols such as xylitol and mannitol; colloidal silica; and mixtures thereof. The co-processed spray dried forms of microcrystalline cellulose and carboxymethyl cellulose sodium have been marketed under the trade names Avicel® RC-501, Avicel® RC-581, Avicel® RC-591, and Avicel® CL-611.

Suitable glidants are selected from the group comprising silica, calcium silicate, magnesium silicate, colloidal silicon dioxide, corn starch, talc, stearic acid, magnesium stearate, calcium stearate, sodium stearyl fumarate, hydrogenated vegetable, and mixtures thereof.

Suitable sweetening agents are selected from the group comprising saccharine or its salts such as sodium, potassium, or calcium, cyclamate or its salt, aspartame, alitame, acesulfame or its salt, stevioside, glycyrrhizin or its derivatives, sucralose, and mixtures thereof.

Suitable flavors are selected from the group comprising peppermint, grapefruit, orange, lime, lemon, mandarin, pineapple, strawberry, raspberry, mango, passion fruit, kiwi, apple, pear, peach, apricot, cherry, grape, banana, cranberry, blueberry, black currant, red currant, gooseberry, lingon berries, cumin, thyme, basil, camille, valerian, fennel, parsley, chamomile, tarragon, lavender, dill, bargamot, salvia, aloe vera balsam, spearmint, eucalyptus, and combinations thereof.

Suitable coloring agents are selected from the group comprising dyes, natural coloring agents or pigments, approved for use under Federal Food, Drug and Cosmetic Act.

Suitable anti-caking agents are selected from the group comprising colloidal silicon dioxide, tribasic calcium phosphate, powdered cellulose, magnesium trisilicate, starch, and mixtures thereof.

Suitable wetting agents are selected from the group comprising anionic, cationic, nonionic, or zwitterionic surfactants, and combinations thereof. Suitable examples of wetting agents are sodium lauryl sulphate; cetrimide; polyethylene glycols; polyoxyethylene-poly block copolymers such as poloxamers; polyglycerin fatty acid esters such as decaglyceryl monolaurate and decaglyceryl monomyristate; sorbitan fatty acid esters such as sorbitan monostearate; polyoxyethylene sorbitan fatty acid ester such as polyoxyethylene sorbitan monooleate; polyethylene glycol fatty acid ester such as polyoxyethylene monostearate; polyoxyethylene alkyl ether such as polyoxyethylene lauryl ether; polyoxyethylene castor oil; and mixtures thereof.

Suitable preservatives are selected from the group comprising parabens such as methyl, ethyl, propyl, and butyl p-hydroxybenzoic acid esters, alkyl hydroxybenzoates, sorbic acid or a salt thereof, benzoic acid or a salt thereof, salts of edetate (also known as salts of ethylenediaminetetraacetic acid or EDTA, such as disodium edetate), benzalkonium chloride, and mixtures thereof.

Suitable antioxidants are selected from the group comprising butylated hydroxytoluene (BHT), butylated hydroxyanisole (BHA), sodium metabisulfite, ascorbic acid, propyl gallate, thiourea, tocopherols, beta-carotene, and mixtures thereof.

Suitable chelating agents are selected from the group comprising ethylenediamine tetraacetic acid (EDTA) and its salts, such as, for example, dipotassium ethylenediamine tetraacetate, calcium disodium ethylenediamine tetraacetate, tetrasodium ethylenediamine tetranetate, and mixtures thereof.

Suitable binders are selected from the group comprising polyvinyl pyrrolidone, starch, pregelatinized starch, hydroxypropylmethyl cellulose, hydroxyethyl cellulose, methyl cellulose, sodium carboxymethyl cellulose, gums, acrylate polymers, and mixtures thereof.

Suitable viscosity modifiers are selected from the group comprising chitosan, acacia, alginic acid bentonite, carbomers, carboxymethylcellulose calcium or sodium, cetostearyl alcohol, methyl cellulose, ethyl cellulose, glycerin, gelatin guar gum, hydroxyethyl cellulose, hydroxymethyl cellulose, hydroxypropyl cellulose, hydroxypropyl methyl cellulose, any other suitable cellulose-based component, maltodextrin, polyvinyl alcohol, povidone, propylene carbonate, propylene glycol alginate, sodium alginate, starch, sodium starch glycolate, starch tragacanth, xanthan gum, and mixtures thereof.

Suitable emulsifiers include, but are not limited to natural emulsifier, an anionic emulsifier or a nonionic emulsifier. These include, but are not limited to, sodium dodecyl sulfate, sodium octadecyl sulfate, sorbitol anhydrate, tween, and mixtures thereof.

The viscosity of the pharmaceutically acceptable carrier ranges from about 300 cps to about 15,000 cps. Preferably, the viscosity of the carrier ranges from about 500 cps to about 10,000 cps. More preferably, the viscosity of the carrier ranges from about 500 cps to about 7,000 cps. The viscosity of the carrier of the present invention is measured by using a Brookfield Viscometer having a #3 spindle rotating at 20 rpm at 25° C.

The amounts of each excipient can readily be determined or ascertained by the person skilled in the art.

When the liquid composition is an extended release composition, it may additionally comprise an immediate release component for biphasic or pulsatile type of release. Immediate release component may help in providing an immediate therapeutic effect which could be subsequently followed by an extended therapeutic effect over a longer duration of time. In one example, immediate release component may be present the form a powder, pellets, beads, spheroids or granules of guanfacine in the carrier. Alternatively, the immediate release component may be present in the form of an immediate release coating of guanfacine over the extended release coated cores. Alternatively, the immediate release component of guanfacine may be present in form of guanfacine-resin complexes.

The invention also provides for methods of making the compositions described herein by usual methods well known in the art.

Ready-to use liquid compositions may be prepared by the conventional processes comprising dissolving an amount of guanfacine and any other excipients into the pharmaceutically acceptable carrier.

Alternatively, the process comprises preparing cores comprising guanfacine and optionally one or more other pharmaceutically acceptable excipients. These guanfacine containing cores are then coated with a suitable polymer for immediate release or extended release by usual coating techniques. These coated cores are then dispersed in the pharmaceutically acceptable carrier to form ready-to-use liquid composition.

Reconstituted liquid compositions of the present invention may be prepared by the process comprising the steps of forming powder, granules or pellets as dry powder by conventional processes.

The process also includes forming complexes of guanfacine with ion-exchange resins, comprising loading a plurality of resin particles with guanfacine to form drug-resin particles. These particles may optionally be further coated with immediate release or extended release coating using conventional techniques. Methods of loading drugs onto resin particles are generally known in the art.

The ready-to-use liquid compositions of the present invention may be packaged in a suitable package such as a bottle. The dry powder for reconstitution may be packaged in a suitable package such as a bottle or a sachet. Further, the sachet can be filled as a unit dose or a multi dose sachet. The present invention further includes a co-package or a kit comprising two components, wherein one package or one component comprises a dry powder and another package or another component comprises the pharmaceutically acceptable carrier. Alternatively, a twin chamber pack with two chambers can be used. In this case, one chamber comprises a powder for suspension and another chamber comprises the carrier.

The invention also provides for various methods of treatment using the compositions described herein. In a particular embodiment, the invention provides for methods of treating ADHD or hypertension comprising administering an effective amount of any of the composition described herein, wherein the composition is meant for immediate release or extended release or combination of both.

The invention may be further illustrated by the following examples, which are for illustrative purposes only and should not be construed as hunting the scope of the invention in any way.

TABLE 1 pH dependent degradation profile (Guanfacine hydrochloride)-solution state stability

| Time | % Assay | | | | |
|---|---|---|---|---|---|
| (hours) | pH 1.2 | pH 2.2 | pH 4.5 | pH 6.8 | pH 7.5 |
| 0 | 101.2 | 100.3 | 99.4 | 99.5 | 100.9 |
| 1 | 101.2 | 100.5 | 99.0 | 99.0 | 99.9 |
| 4 | 101.2 | 100.4 | 98.7 | 97.2 | 97.1 |
| 8 | 101.1 | 100.4 | 98.9 | 93.7 | 92.2 |
| 16 | 101.6 | 100.3 | 98.7 | 86.3 | 84.0 |
| 24 | 101.4 | 100.2 | 98.5 | 79.9 | 77.5 |

As can be seen from the above Table 1, the assay values of guanfacine are substantially decreasing over time at high pH values, clearly indicating decreased stability of guanfacine at high pH. On the other hand, no major changes in assay values of guanfacine were observed in acidic conditions over time, indicating guanfacine is stable at lower pH values.

Example 1-2: Comparative Compositions of Guanfacine

|  | Quantity/unit (in mg) | |
| --- | --- | --- |
| Ingredients | Example 1 | Example 2- Comparative Example |
| Guanfacine hydrochloride | 1.15 | 1.15 |
| Citric acid | 1.40 | 0.00 |
| Xylitol | 690.00 | 690.00 |
| Water | q.s. to 1 mL | q.s. to 1 mL |

Procedure:

Guanfacine hydrochloride, xylitol, citric acid (in Example 1) were mixed in water to form liquid compositions.

Stability Studies

The compositions prepared as per Example 1 and Example 2 (Comparative Example) were stored at room temperature and the samples were analyzed after 3 days and 7 days. Stability results are represented in Table 2 below.

TABLE 2

Stability data of compositions prepared as per Example 1 and Example 2

| Impurities/ Related substances (RS) (% w/w) | ICH Specification | Example 1 | Example 2- Comparative Example |
| --- | --- | --- | --- |
| 3 days- Room temperature | | | |
| 2,6-Dichlorophenylacetic acid | NMT 0.7 | 0.02 | 0.13 |
| Highest Unknown Impurity | NMT 0.5 | 0.00 | 0.87 |
| Total RS | NMT 2.0 | 0.02 | 1.76 |
| 7 days- Room temperature | | | |
| 2,6-Dichlorophenylacetic acid | NMT 0.7 | 0.06 | 0.14 |
| Highest Unknown Impurity | NMT 0.5 | 0.03 | 0.87 |
| Total RS | NMT 2.0 | 0.11 | 1.24 |

As seen from the above Table 2, it is observed that the amounts of impurity 2,6-dichlorophenyl acetic acid and total related substances was significantly reduced in composition having an acid as compared to the composition without an acid. Hence, it is clear that inclusion of an acid enhanced the stability of guanfacine.

Examples 3-5: Compositions of Guanfacine with Different Acids

|  | Quantity/unit (in mg) | | |
| --- | --- | --- | --- |
| Ingredients | Example 3 | Example 4 | Example 5 |
| Guanfacine hydrochloride | 1.15 | 1.15 | 1.15 |
| Fumaric acid | 3.5 | — | — |
| Tartaric acid | — | 3.5 | — |
| Citric acid | — | — | 3.5 |
| Water | q.s. to 1 mL | q.s. to 1 mL | q.s. to 1 mL |

Procedure:

Guanfacine hydrochloride, suitable acid (fumaric/tartaric/citric acids) were mixed in water to form liquid compositions.

Stability Studies

The compositions prepared as per Examples 3-5 were stored at room temperature and the samples were analyzed after 30 days. Stability results are represented in Table 3 below.

TABLE 3

Stability data of compositions prepared as per Examples 3-5

| Impurities/ Related substances (RS) (% w/w) | ICH Specification | Example 3 | Example 4 | Example 5 |
| --- | --- | --- | --- | --- |
| | | 30 days- Room temperature | | |
| 2,6-Dichlorophenylacetic acid | NMT 0.7 | 0.23 | 0.22 | 0.27 |
| Highest Unknown Impurity | NMT 0.5 | 0.05 | 0.04 | 0.04 |
| Total RS | NMT 2.0 | 0.31 | 0.28 | 0.32 |

As seen from the above Table 3, equivalent stability results have been obtained with all the three studied acids i.e. fumaric acid, tartaric acid and citric acid.

Examples 6-8: Guanfacine Extended Release Powder for Suspension Compositions

|  | Quantity/unit (in mg) | | |
| --- | --- | --- | --- |
| Ingredients | Example 6 | Example 7 | Example 8 |
| Drug layered core | | | |
| Microcrystalline cellulose spheres | 30.00 | 30.00 | 30.00 |
| Guanfacine hydrochloride | 1.15 | 1.15 | 1.15 |
| Hydroxypropylmethyl cellulose | 4.00 | 4.00 | 4.00 |
| Citric acid | 0.02 | 0.2 | 0.50 |
| Mannitol | 3.00 | 3.00 | 3.00 |
| Purified water | q.s. | q.s. | q.s. |
| Extended release (ER) coated core | 35% w/w coating | 35% w/w coating | 44.26% w/w coating |
| Ethyl cellulose | 12.02 | 12.08 | 15.40 |
| Dibutyl sebacate | 1.33 | 1.34 | 1.71 |
| Acetone | q.s. | q.s. | q.s. |
| Purified water | q.s. | q.s. | q.s. |
| Weight of ER coated core | 51.52 | 51.77 | 55.76 |
| Carrier composition | | | |
| Microcrystalline cellulose - sodium carboxymethyl cellulose (Avicel ® CL-611) | 20.00 | 20.00 | 20.00 |
| Xanthan gum | 1.50 | 1.50 | 1.50 |
| Colloidal silicon dioxide | 3.50 | 3.50 | 3.50 |
| Sucralose | 0.50 | 0.50 | 0.50 |
| Xylitol | 450.00 | 450.00 | 450.00 |
| Strawberry flavor | 2.00 | 2.00 | 2.00 |
| Citric acid | 1.40 | 1.40 | 1.40 |
| Methyl paraben | — | 1.80 | 1.80 |
| Propyl paraben | — | 0.20 | 0.20 |
| Purified water | q.s. to 1 mL | q.s. to 1 mL | q.s. to 1 mL |

Procedure:

1. Citric acid, mannitol, hydroxypropylmethyl cellulose, guanfacine hydrochloride were dissolved in purified water.

2. Microcrystalline cellulose spheres were coated with the solution of step 1.

3. Ethyl cellulose and dibutyl sebacate were dispersed in a mixture of acetone and purified water.

4. The drag layered cores of step 2 were coated with the coating dispersion of step 3 to form extended release powder for suspension.

5. Microcrystalline cellulose—sodium carboxymethyl cellulose, xanthan gum, colloidal silicon dioxide, sucralose, xylitol, strawberry flavor, citric acid, methyl/propyl paraben (if present) were mixed in purified water to form the pharmaceutically acceptable carrier.

6. The extended release powder for suspension and the pharmaceutical': acceptable carrier were separately packed in a twin chamber pack.

Stability Studies

The extended release powder for suspension compositions prepared as per Examples 7 and 8 were stored at 40° C./75% RH for 3 months and 1 month respectively. Thereafter, the powder for suspension was reconstituted with the carrier and the amounts of impurity 2,6-dichlorophenyl acetic acid and total related substances was determined. The initial levels of impurities/related substances and levels after 3 months/1 month are represented in Table 4 below.

TABLE 4

Stability data of the reconstituted liquid compositions prepared as per Examples 7-8

| Impurities/ Related substances (RS) (% w/w) | ICH Specification | Example 7 | | Example 8 | |
|---|---|---|---|---|---|
| | | Initial | 40° C./ 75% RH- 3 M | Initial | 40° C./ 75% RH- 1 M |
| 2-6 Dichlorophenyl acetic acid | NMT 0.7 | 0.03 | 0.22 | 0.00 | 0.06 |
| Highest Unknown | NMT 0.5 | 0.05 | 0.03 | 0.03 | 0.02 |
| Total RS | NMT 2.0 | 0.14 | 0.34 | 0.03 | 0.08 |

In-Vitro Studies

The extended release powder for suspension prepared as per Examples 6 and 8 was reconstituted with the carrier and the in-vitro dissolution was determined for 4 mg dose at day 0 using USP type II apparatus at 75 rpm, in 900 mL of hydrochloric acid buffer with pH 2.2 at 37° C. The results of the release studies are represented in Table 5.

TABLE 5

Percentage (%) of guanfacine release from reconstituted compositions prepared as per Examples 6 and 8 in 900 mL hydrochloric acid buffer pH 2.2, USP type II, 75 rpm

| | Percentage (%) of guanfacine release | |
|---|---|---|
| Time (hours) | Example 6 | Example 8 |
| 1 | 18 | 11 |
| 2 | 38 | 29 |
| 4 | 58 | 54 |
| 6 | 68 | 68 |
| 12 | 79 | 83 |
| 16 | 83 | 87 |

TABLE 5-continued

Percentage (%) of guanfacine release from reconstituted compositions prepared as per Examples 6 and 8 in 900 mL hydrochloric acid buffer pH 2.2, USP type II, 75 rpm

| | Percentage (%) of guanfacine release | |
|---|---|---|
| Time (hours) | Example 6 | Example 8 |
| 20 | — | 90 |
| 24 | — | 92 |

Examples 912: Guanfacine Extended Release Powder for Suspension Compositions

| | Quantity/unit (in mg) | | | |
|---|---|---|---|---|
| Ingredients | Example 9 | Example 10 | Example 11 | Example 12 |
| Drug layered core | | | | |
| Microcrystalline cellulose spheres | 30.00 | 30.00 | 30.00 | 30.00 |
| Guanfacine hydrochloride | 1.15 | 1.15 | 1.15 | 1.15 |
| Hydroxypropylmethyl cellulose | 4.00 | 4.00 | 4.00 | 4.00 |
| Citric acid | 0.50 | 0.50 | 0.50 | 0.50 |
| Mannitol | 3.00 | 3.00 | 3.00 | 3.00 |
| Purified water | q.s. | q.s. | q.s. | q.s. |
| Extended release (ER) coated core | | 44.26% w/w coating | | |
| Ethyl cellulose | 15.4 | 15.4 | 15.4 | 15.4 |
| Dibutyl sebacate | 1.71 | 1.71 | 1.71 | 1.71 |
| Acetone | q.s | q.s | q.s | q.s |
| Purified water | q.s. | q.s. | q.s. | q.s. |
| Weight of ER coated core | 55.76 | 55.76 | 55.76 | 55.76 |
| Carrier composition | | | | |
| Xylitol | 690.00 | 300.00 | 495.00 | 690.0 |
| Citric acid | 0.50 | 5.00 | 2.75 | 5.00 |
| Purified water | q.s. to 1 mL | q.s. to 1 mL | q.s. to 1 mL | q.s. to 1 mL |

Procedure:

1. Citric acid, mannitol, hydroxypropylmethyl cellulose, guanfacine hydrochloride were dissolved in purified water.

2. Microcrystalline cellulose spheres were coated with the solution of step 1.

3. Ethyl cellulose and dibutyl sebacate were dispersed in a mixture of acetone and purified water.

4. The drag layered cores of step 2 were coated with the coating dispersion of step 3 to form extended release powder for suspension.

5. Xylitol and citric acid were mixed in purified water to form the pharmaceutically acceptable carrier.

6. The extended release powder for suspension was reconstituted with the pharmaceutically acceptable carrier and packed in a suitable container.

Stability Studies

The compositions prepared as per Examples 9-12 were stored at room temperature for 30 days. After 30 days, the amounts of impurity 2,6-dichlorophenyl acetic acid and total related substances was determined. The results are represented in Table 6 below.

TABLE 6

Stability data of the reconstituted liquid compositions prepared as per Examples 9-12

| Impurities/ Related substances (RS) (% w/w) | ICH Specification | Example 9 | Example 10 | Example 11 | Example 12 |
|---|---|---|---|---|---|
| | | 30 days- Room Temperature | | | |
| 2,6-Dichlorophenylacetic acid | NMT 0.7 | 0.11 | 0.13 | 0.12 | 0.09 |
| Highest Unknown | NMT 0.5 | 0.05 | 0.05 | 0.05 | 0.04 |
| Total RS | NMT 2.0 | 0.16 | 0.18 | 0.17 | 0.13 |

In-Vitro Studies

The powder for suspension compositions prepared as per Examples 9-11 was stored for 10 days/30 days. After 10 days/30 days, the in-vitro dissolution was determined for 4 mg dose using USP type II apparatus at 75 rpm, in 900 mL of hydrochloric acid buffer with pH 2.2 at 37° C. The results of the release studies are represented in Table 7 below.

TABLE 7

Percentage (%) of guanfacine release from reconstituted liquid compositions prepared as per Examples 9-11 in hydrochloric acid buffer pH 2.2, USP type II, 75 rpm, 900 ml

| Time | Percentage (%) of Guanfacine Release | | | | | |
|---|---|---|---|---|---|---|
| | Example 9 | | Example 10 | | Example 11 | |
| (hours) | 10 days | 30 days | 10 days | 30 days | 10 days | 30 days |
| 1 | 12 | 14 | 25 | 27 | 18 | 21 |
| 2 | 29 | 31 | 37 | 39 | 33 | 35 |
| 4 | 51 | 52 | 55 | 56 | 54 | 55 |
| 6 | 65 | 65 | 67 | 68 | 67 | 67 |
| 12 | 83 | 82 | 83 | 83 | 84 | 83 |
| 16 | 88 | 87 | 88 | 88 | 88 | 87 |
| 20 | 90 | 90 | 90 | 91 | 91 | 90 |
| 24 | — | 92 | — | 93 | — | 92 |

Examples 13-14: Guanfacine Extended Release Powder for Suspension Compositions

| Ingredients | Quantity/unit (in mg) | |
|---|---|---|
| | Example 13 | Example 14 |
| Drug Layered core | | |
| Microcrystalline cellulose spheres | 30.00 | 30.00 |
| Guanfacine hydrochloride | 1.15 | 1.15 |
| Hydroxypropylmethyl cellulose | 4.00 | 4.00 |
| Citric acid | 0.50 | 0.50 |
| Mannitol | 2.00 | 2.00 |
| Purified water | q.s. | q.s. |
| Extended release (ER) coated core | 50% w/w coating | 42.86% w/w coating |
| Ethyl cellulose | 16.94 | 14.52 |
| Dibutyl sebacate | 1.88 | 1.61 |
| Acetone | q.s. | q.s. |
| Purified water | q.s. | q.s. |
| Weight of ER coated core | 56.47 | 53.78 |
| Carrier composition | | |
| Microcrystalline cellulose - sodium carboxymethyl cellulose (Avicel ® CL-611) | 20.00 | 20.00 |
| Xanthan gum | 2.50 | 1.50 |
| Colloidal silicon dioxide | 3.50 | 3.50 |
| Sucralose | 0.50 | 0.50 |
| Xylitol | 550.00 | 550.00 |
| Strawberry flavor | 2.00 | 2.00 |
| Citric acid | 1.40 | 1.40 |
| Methyl paraben | 1.80 | 1.80 |
| Propyl paraben | 0.20 | 0.20 |
| Purified water | q.s. to 1 mL | q.s. to 1 mL |

Procedure:

1. Citric acid, mannitol, hydroxypropyl methylcellulose, guanfacine hydrochloride were dissolved in purified water.
2. Microcrystalline cellulose spheres were coated with the solution of step 1.
3. Ethyl cellulose and dibutyl sebacate were dispersed in a mixture of acetone and purified water.
4. The drug layered cores of step 2 were coated with the coating dispersion of step 3 to form extended release powder for suspension.
5. Microcrystalline cellulose—sodium carboxymethyl cellulose, xylitol, citric acid, xanthan gum, colloidal silicon dioxide, sucralose, strawberry flavor, methyl paraben and propyl paraben were mixed in purified water to form the pharmaceutically acceptable carrier.
6. The extended release powder for suspension and the pharmaceutically acceptable carrier were separately packed in a twin chamber pack.

Stability Studies

The extended release powder for suspension composition prepared as per Example 14 was stored at 40° C./75% RH for one month. After one month, the powder for suspension was reconstituted with the carrier and the amounts of impurity 2,6-dichlorophenyl acetic acid and total related substances was determined. The initial levels of impurities/related substances and levels after 1 month are represented in Table 8 below.

TABLE 8

Stability data of reconstituted liquid compositions prepared as per Example 14

| Impurities/ Related substances (RS) (% w/w) | ICH Specification | Example 14 | |
|---|---|---|---|
| | | Initial | 40° C./ 75% RH - 1 M |
| 2-6 Dichlorophenyl acetic acid | NMT 0.7 | 0.01 | 0.10 |
| Highest Unknown | NMT 0.5 | 0.03 | 0.03 |
| Total RS | NMT 2.0 | 0.10 | 0.16 |

In-Vitro Studies

The extended release powder for suspension prepared as per Example 14 was stored at 40° C./75% RH for one month. After one month, the in-vitro dissolution was determined for 4 mg dose using USP type II apparatus at 75 rpm, in 900 mL of hydrochloric acid buffer with pH 2.2 at 37° C. The results of the initial release studies and after 1 month are represented in Table 9 below.

TABLE 9

Percentage (%) of guanfacine release from extended release powder for suspension prepared as per Example 14 in 900 mL of hydrochloric acid buffer, pH 2.2, USP type II, 75 rpm

| Time (hours) | Percentage (%) of guanfacine release | |
|---|---|---|
| | Initial | 40° C./75% RH - 1 M |
| 1 | 19 | 22 |
| 2 | 33 | 36 |
| 4 | 46 | 50 |
| 6 | 55 | 59 |
| 12 | 68 | 74 |
| 16 | 73 | 79 |
| 20 | 76 | 82 |
| 24 | 79 | 84 |

Core Size Measurements

The sizes of the guanfacine layered cores and the extended release coated cores prepared as per Example 14 were measured by Camsizer and the results are provided in Table 10 below:

TABLE 10

Core sizes

| Sample | Core sizes |
|---|---|
| Guanfacine layered core (without ER coating) | $d_{90} = 0.255$ mm<br>$d_{50} = 0.187$ mm<br>$d_{10} = 0.141$ mm |
| Extended release coated core | $d_{90} = 0.349$ mm<br>$d_{50} = 0.239$ mm<br>$d_{10} = 0.181$ mm |

Viscosity Measurements

Viscosity of the carrier prepared as per Example 14 was measured by Brookfield viscometer. The values are provided in Table 11 below.

TABLE 11

Viscosity measurements

| Sample | Results |
|---|---|
| Viscosity of the carrier as per Example 14 | Spindle 3<br>rpm = 20<br>% torque = 18.1%,<br>Viscosity = 905 cps |

Example 15: Guanfacine Extended Release Powder for Suspension Compositions

| Ingredients | Quantity/unit (in mg) |
|---|---|
| Drug layered core | |
| Microcrystalline cellulose spheres | 30.00 |
| Guanfacine hydrochloride | 1.15 |
| Citric acid | 0.50 |
| Eudragit ®L 100-55 | 1.50 |
| Triethyl citrate | 0.15 |
| Talc | 0.45 |
| Acetone | q.s. |
| Purified water | q.s. |
| Extended release (ER) coated core | 15% w/w coating |
| Ethyl cellulose | 4.56 |
| Dibutyl sebacate | 0.51 |
| Acetone | q.s. |
| Purified water | q.s. |
| Weight of ER coated core | 38.82 |
| Carrier composition | |
| Microcrystalline cellulose - sodium carboxymethyl cellulose (Avicel ® CL-611) | 40.00 |
| Xanthan gum | 2.50 |
| Aerosil | 3.50 |
| Sucralose | 0.50 |
| Xylitol | 550.00 |
| Strawberry flavor | 2.00 |
| Citric acid | 1.40 |
| Methyl paraben | 1.80 |
| Propyl paraben | 0.20 |
| Purified water | q.s. to 1 mL |

Procedure:

1. Citric acid, Eudragit® L 100-55, triethyl citrate, talc, guanfacine hydrochloride were dispersed in a mixture of acetone and purified water.
2. Microcrystalline cellulose spheres were coated with the dispersion of step 1.
3. Ethyl cellulose and dibutyl sebacate were dispersed in a mixture of acetone and purified water.
4. The drug layered cores of step 2 were coated with the coating dispersion of step 3 to form extended release powder for suspension.
5. Microcrystalline cellulose sodium carboxymethyl cellulose, xylitol, citric acid, xanthan gum, colloidal silicon dioxide, sucralose, strawberry flavor, methyl paraben and propyl paraben were mixed in purified water to form the pharmaceutically acceptable carrier.
6. The extended release powder for suspension and the pharmaceutically acceptable carrier were separately packed in a twin chamber pack.

Example 16: Guanfacine Ready-To-Use Oral Liquid Composition

| Ingredients | Quantity/unit (in mg) |
|---|---|
| Drug layered core | |
| Guanfacine hydrochloride | 1.15 |
| Hydroxypropyl methyl cellulose | 4.00 |
| Microcrystalline cellulose spheres | 30.00 |
| Mannitol | 2.00 |
| Citric Acid | 0.50 |
| Purified water | q.s. |
| Carrier composition | |
| Microcrystalline cellulose - sodium carboxymethyl cellulose (Avicel ® CL-611) | 20.00 |
| Xanthan gum | 1.50 |
| Colloidal silicon dioxide | 3.50 |
| Sucralose | 0.50 |
| Xylitol | 550.00 |
| Strawberry flavor | 2.00 |
| Citric acid | 1.40 |
| Methyl Paraben | 1.80 |
| Propyl Paraben | 0.20 |
| Purified water | q.s. to 1 mL |

Procedure:

1. Dissolve citric acid, mannitol, hydroxypropyl methyl cellulose, and guanfacine hydrochloride in purified water under stirring to get clear solution.

2. Spray the solution obtained from step 1 onto microcrystalline cellulose spheres.

3. Mix microcrystalline cellulose—sodium carboxymethyl cellulose, xanthan gum, colloidal silicon dioxide, sucralose, xylitol, strawberry flavor, citric acid, methyl paraben, propyl paraben under stirring to make a uniform dispersion in purified water, to form the pharmaceutically acceptable carrier.

4. Pack separately drug layered cores and the carrier in a twin chamber pack.

We claim:

1. A stable extended release oral liquid composition of guanfacine comprising guanfacine in a concentration from about 0.1 mg/ml to about 7.0 mg/mL of the composition and
   i) a core in the form of bead, pellets, granule, or spheroid comprising guanfacine and an acid;
   ii) a coating over the core comprising a pH independent release-controlling agent; and
   iii) a pharmaceutically acceptable carrier comprising one or more of liquid adjuvants;
   wherein the liquid composition comprises less than about 3.0% w/w of total related substances when stored at 40° C. and 75% relative humidity (RH) for at least 3 months and guanfacine is not present as guanfacine-resin complex.

2. The stable extended release oral liquid composition of claim 1, wherein the composition comprises less than about 1.0% w/w of 2,6-dichlorophenyl acetic acid.

3. The stable extended release oral liquid composition of claim 2, wherein the composition comprises less than about 0.7% w/w of 2,6-dichlorophenyl acetic acid.

4. The stable extended release oral liquid composition of claim 1, wherein the composition comprises less than about 2.0% w/w of total related substances when stored at 40° C. and 75% RH for at least 3 months.

5. The stable extended release oral liquid composition of claim 1, wherein the composition has a pH of less than about 6.8.

6. The stable extended release oral liquid composition of claim 1, wherein the composition is a ready-to-use liquid composition or a reconstituted liquid composition.

7. The stable extended release oral liquid composition of claim 6, wherein the ready-to-use liquid composition comprises a solution, a suspension, a syrup, a concentrate, an elixir, or an emulsion.

8. The stable extended release oral liquid composition of claim 1, wherein guanfacine is present in the core or layered over an inert particle to form a core.

9. The stable extended release oral liquid composition of claim 1, wherein the pH-independent release-controlling agent is selected from the group consisting of cellulosic polymers; acrylic copolymers; polyethylene derivatives; polyvinyl alcohol; polyvinyl acetate; gums; triglycerides; waxes; lipids; fatty acids or their salts/derivatives; polyvinyl polymers; polyvinyl acetate and polyvinyl pyrrolidone mixtures; and combinations thereof.

10. The stable extended release oral liquid composition of claim 1, wherein the core further comprises pharmaceutically acceptable excipients selected from the group consisting of osmogents, binders, glidants, and combinations thereof.

11. The stable extended release oral liquid composition of claim 1, wherein the composition further comprises guanfacine in an immediate release form.

12. The stable extended release oral liquid composition of claim 1, wherein the pharmaceutically acceptable carrier further comprises acids, osmogents, buffering agents, suspending agents, glidants, sweetening agents, flavors, colorants, anti-caking agents, wetting agents, preservatives, antioxidants, chelating agents, binders, viscosity modifiers, emulsifiers and combinations thereof.

* * * * *